United States Patent
Staehlin et al.

[19]

[11] Patent Number: 5,954,673
[45] Date of Patent: Sep. 21, 1999

[54] METHOD AND APPARATUS FOR ORAL MOTOR THERAPY USING A VISUAL DISPLAY

[75] Inventors: John H. Staehlin, Lutherville; Jack Light, Rockville; Warren O'Reilly, Ellicott City; Dan Buck, Hanover; John Knight, Ellicott City; Mike Robinson, Severna Park; Erick Figueroa, Crofton; Forest Platt, Columbia; Phil Atkinson, Baltimore, all of Md.

[73] Assignee: Volunteers for Medical Engineering, Baltimore, Md.

[21] Appl. No.: 08/907,006

[22] Filed: Aug. 6, 1997

[51] Int. Cl.$^6$ .................................................. A61B 5/103
[52] U.S. Cl. ........................... 600/590; 600/587; 433/68; 433/71; 73/379.02; 73/862.68; 482/11
[58] Field of Search ............................... 482/11; 600/590; 433/68, 69, 71; 606/234, 235; 73/862.381, 379.02, 379.03; 310/338

[56] References Cited

U.S. PATENT DOCUMENTS

| | | | |
|---|---|---|---|
| 1,427,496 | 8/1922 | Ono | 73/379.02 X |
| 1,706,179 | 3/1929 | McBean | 73/379.02 X |
| 3,297,021 | 1/1967 | Davis | 73/379.02 X |
| 3,349,489 | 10/1967 | Shakelford | 433/68 |
| 4,112,596 | 9/1978 | Fletcher et al. | |
| 4,390,028 | 6/1983 | Okano | 600/595 |
| 4,402,326 | 9/1983 | Okano | 600/595 |
| 4,488,873 | 12/1984 | Bloomfield | 433/71 |
| 4,521,186 | 6/1985 | Wodlinger | 433/71 |
| 4,592,727 | 6/1986 | Bloomfield | 433/71 |
| 4,821,584 | 4/1989 | Lembke | 73/862.68 X |
| 4,856,993 | 8/1989 | Maness | 433/68 |
| 5,213,553 | 5/1993 | Light | |
| 5,395,239 | 3/1995 | Komatsu | 433/68 |
| 5,452,727 | 9/1995 | Tura | 600/595 |

FOREIGN PATENT DOCUMENTS

1130-334  12/1984  U.S.S.R. .................................. 433/68

OTHER PUBLICATIONS

Home Automation Newsletter, *Independence and Esthetics: A Consumer's Perspective*, Jan., 1995.
New Abilities Marketing Information, *USC 1000™ with TongueTouch Keypad™*, Jul. 11, 1994.
Articulation: A Physiological Approach, *Electropalatography*, pp. 72–78, p. 274.
Clinical Measurement of Speech and Voice, *Electropalatography*, pp. 442–445.

*Primary Examiner*—Richard J. Apley
*Assistant Examiner*—William LaMarca
*Attorney, Agent, or Firm*—Finnegan, Henderson, Farabow, Garrett & Dunner

[57] ABSTRACT

A method for determining muscle strength of elements of the musculature used in speech and swallowing. In particular, a tool is equipped with at least one pressure sensor. A person inserts the tool into the person's mouth and utters sounds of speech or swallows. While uttering sounds of speech or swallowing, portions of the oral musculature contact and exert force on the sensor. A representation of this force is displayed at a visual display device as an indication of muscle strength and position.

7 Claims, 3 Drawing Sheets

METHOD AND APPARATUS FOR ORAL MOTOR THERAPY USING A VISUAL DISPLAY

The present invention relates generally to oral motor therapy for individuals with oral motor disorders. Specifically, this invention provides a system that enables patients and their therapists, while performing a designed exercise program, to visually monitor their progress toward overcoming oral motor disorders.

People who suffer from head trauma, oral cancer, oral surgery, infant deafness, or strokes may develop speech and swallowing impediments (hereinafter "oral motor" or "motor skills"). In the past, therapy for these impediments included intraoral prosthesis to compensate for lost motor skills and/or missing oral anatomy. These prostheses were custom designed for individual patients. When combined with the performance of exercise protocols or programs, patients could treat their oral motor dysfunctions.

In order to reduce costs and improve oral motor therapy for patients suffering from, for example, head traumas or stokes, a procedure was developed using a series of generic handheld intraoral prostheses. These devices are not individually designed prostheses uniquely fitted to each patient's mouth, but rather generic exercise tools. These tools generally comprise a series of handheld tactile aids (exercise tools) designed to fit the average adult mouth. For a complete description of the aids see U.S. Pat No. 5,213,553, issued to Jack Light, the disclosure of which is incorporated herein by reference. A patient uses these tools to exercise the tongue, cheeks, and lips. For example, to exercise the lips, a patient or a therapist would hold an exercise tool by its handle and place the palatal portion against the upper palate. Then, following a doctor's or therapist's directions, the patient would perform an exercise to strengthen, for example, the lip muscles. The exercise uses the shape of the exercise tool to strengthen the muscle. The exercise tool shape is especially designed to assist a patient in placing his lips in the proper position for forming sounds or swallowing and by pushing against the shape of the tool, and using an exercise protocol the lip muscle can be strengthened.

The exercise program enables patients to treat oral motor disorders using tactile or touch feedback in addition to auditory feedback. The present invention enables patients and therapists to use additionally visual feedback. By providing a visual feedback display system to increase the level of information available to a patient, the rehabilitation process accelerates.

SUMMARY OF THE INVENTION

Advantages achieved by the invention will be set forth in part in the description which follows, and in part will be obvious from the description, or may be learned by practice of the invention. The advantages of the invention will be realized and attained by means of the elements and combinations particularly pointed out in the appended claims.

To attain the advantages and in accordance with the purpose of the invention, as embodied and broadly described herein, apparatus consistent with the present invention provide improved methods of monitoring and displaying the muscle activation, movement, and strength of oral musculature used during the utterance of sound or during the process of swallowing. Specifically, the present invention comprises a method for determining the movement patterns and muscle strength of oral musculature used while speaking and swallowing. The method comprises providing a tool specifically shaped to evaluate musculature that is under investigation. This tool is equipped with one or more pressure sensors strategically located to be acted upon by the oral musculature under investigation when the tool is inserted into a person's mouth. The sensor in the tool measures forces applied to it while the person performs the desired anatomical effort such as movement, contact, and force applied by the musculature during the act of swallowing or the utterance of speech sounds. When contacted by oral musculature, the associated sensor provides an electrical output that is proportional to the applied pressure or force. The electrical output is, therefore, a measure of the muscle strength associated with the element of the oral anatomy under scrutiny and also a measure of the correct placement of muscle pressure. This electrical signal is then applied to a control and display device which provides a visual feedback to the person being evaluated and/or the attending therapist of the placement and the applied pressure. The display thereby provides a visual indication of relative muscle strength and oral musculature contact.

Another aspect of the present invention is an oral motor therapy system comprising a speech therapy tool that includes a handle connected to a mouthpiece configured for insertion into a person's mouth. The tool has at least one pressure sensor located at the base of the handle at a position to be contacted by the lips during utterance of speech sounds or during the process of swallowing. The output of the pressure sensor is an electrical signal proportional to the contact pressure. The signal proportional to the contact pressure of the oral musculature is applied to a display and control device to provide a visual indication of muscle strength. The display can be calibrated to permit the muscle force/strength measurements to be evaluated. Additionally, the display can be used to establish a "standard" of correct performance and can be used to measure actual performance relative to the standard.

DESCRIPTION OF THE PREFERRED EMBODIMENT

Reference will now be made in detail to the present preferred embodiments of the invention, examples of which are illustrated in the accompanying drawings. It, is intended that all matter contained in the following description or shown in the accompanying drawings shall be interpreted as illustrative and not in a limiting sense.

The present invention relates specifically to a method and apparatus for supplying visual information to a patient or therapist during treatment and analysis of oral motor dysfunctions. While the disclosure that follows focuses on speech therapy, one of ordinary skill in the art would now appreciate that oral motor therapy tools consistent with the present invention could be used for therapy of not only speech but also swallowing, drooling, mastication, tongue thrusting, etc.

Figure 1:
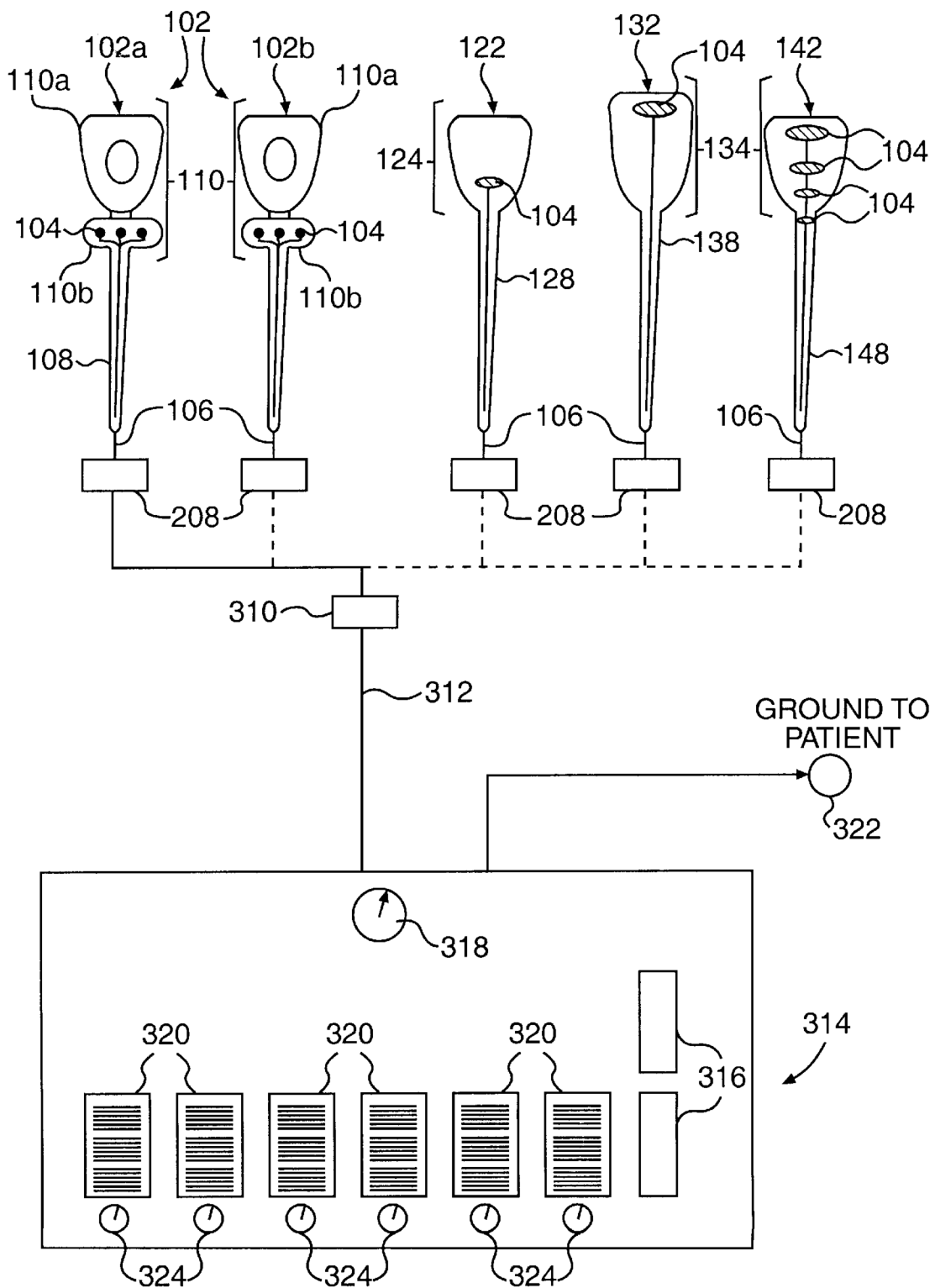
FIG. 1 is a diagram of an oral motor therapy system in accordance with one embodiment of the present invention.

Visual display systems, consistent with the present invention, present information relating to the application and strength of various muscle groups that are involved in speech and swallowing. As shown in FIG. 1, and in accordance with a feature of the present invention, exercise tools 102, 122, 132, and 142 are equipped with one or more pressure sensors 104. These sensors 104 are positioned in exercise tools 102, 122, 132, and 142 at strategic locations where, with the exercise tools correctly inserted into the patient's mouth, the tongue or lips forcibly contact the tools during articulation of various sounds associated with consonants, or where they forcibly contact the tools during the process of swallowing. Each sensor 104 is coupled by leads 106 to a connector (male or female) 208. When pressure sensor 104 is a capacitive coupling type of sensor, a connection must be made to the patient through connector 322. However, it will be appreciated that a variety of sensors may be integrated into an IC chip including a transmitter adapted to provide wireless transmission of pressure-indicating signals. The pressure sensor/transducer for such an IC chip monitor could employ a strain gage (not shown), or equivalent, in place of a capacitive coupling sensor. Such an implementation eliminates the need for leads 106 and connector 322.

As seen in FIG. 1 exercise tool 102 comprises a mouth piece 110, including a palate portion 110a and a lip portion 110b, and a handle 108. Lip portion 110b is equipped with a plurality of sensors 104 positioned to sense lip pressure (i.e., the strength of muscles that moves the lips) and the location of the applied pressure. Preferably sensors 104 are mounted on both sides of lip portion 110b, as indicated by reference numerals 102a and 102b to sense contact pressures exerted by the upper and lower lips. Sensors 104 are strategically located in lip portion 110b to measure lip pressures exerted on the sensors while the patient utters sounds, such as, for example, the consonant /p/.

Exercise tool 122, comprises a mouth piece 124, which is contoured for placement against the palate, and a connecting handle 128. At least one sensor 104 is strategically located in mouth piece 124 of exercise tool 122 to sense contact pressure exerted by the tip of the tongue (i.e., the strength of the muscle that moves the tip of the tongue). This tongue pressure is associated with making sounds such as, for example, the consonant /t/.

Exercise tool 132, comprises a palate-contoured mouth piece 134 and a connecting handle 138. In exercise tool 132, sensor 104 is strategically located in mouth piece 134 to measure the pressure exerted by elevation of the back of the tongue (i.e., the strength of the muscle that moves the back of the tongue). This tongue pressure is involved in uttering sounds such as, for example, the consonant /k/.

Finally, exercise tool 142 comprises a palate-conforming mouth piece 144 and connecting handle 148. A plurality of sensors 104 are mounted in mouth piece 144 and handle 148 to measure the placement and pressure associated with the lips and tongue (both back and tip) during exercise programs requiring use of all the muscles associated with producing speech such as puh, tuh, and kuh.

A control and display device 314, as also shown in FIG. 1, when employed with the capacitive coupling sensor is equipped with a sensor exciter (not shown in FIG. 1), calibration controls 324 for each sensor 104, and an overall sensitivity level dial 318 together with a ±9 volt power source 316 and associated power switch and indicator. Connections are made to each exercise tool 102, 122, 132, and 142 through an external connector 310, and to the patient with connector 322. Connector 310 is matched with one of the connectors 208 to couple control and display device 314 with one of exercise tools 102, 122, 132, or 142. If, however, sensors 104 are capable of wireless transmission, then control and display device 314 would be equipped with one or more receivers for receiving wireless transmissions. Connector 322 provides connection to the patient (not shown). Connector 322 may be to the patient's wrist through a wrist strap (not shown). Alternatively, connector 322 may be a metal knob, or the like, that is held by the patient.

In the preferred embodiment, which employs a capacitive coupling sensor, the control and display device 314 is powered by two 9 volt batteries 316 to assure the safety of the patient when connecting control and display device 314 to the body and mouth of the patient. Alternatively, connection to a utility AC power source is possible if adequate safety precautions are provided in isolating the excitation signal from the power mains.

As indicated above, control and display device 314 has sensitivity level dial 318, LED bargraph displays 320, and calibration controls 324. In particular, control and display device 314 has at least one LED bargraph display 320 and calibration control 324 for each sensor 104 on any given exercise tool 102, 122, 132, or 142. Because exercise tool 102 has six sensors 104, control and display device 314 has six LED bargraph displays 320 and six calibration controls 324. LED bargraph display 320 provides visual indications of lip and tongue contact pressures indicative of the patient's performance of oral motor functions. Sensitivity level dial 318 adjusts the scale factor of the visual display of the sensor signals connected into control and display device 314. In other words, the number of elements of the LED bargraph of each of the individual displays that emit light for a given sensor signal magnitude, and thereby provides a visual indication of the pressure applied by the lips and tongue.

While display device 314 is shown with a single connector 310 for mating with tool connectors 208, one at a time, multiple connectors 310 may be provided to accommodate concurrent connections of all of the tools to device 314. In this case, a selector switch (not shown) would be provided to switch to the particular tool being employed by the patient. Additionally, rather than multiple LED bargraph displays 320, the system could use a single LED bargraph display and a selector switch to select which one of the multiple sensors 104 of a particular tool is displayed by control and display device 314. Notwithstanding these alternative examples, other embodiments or options, such as, for example, audible tones, are equally acceptable and these possible alternatives are simply mentioned as possible variations on the preferred embodiment of the invention.

Figure 2:
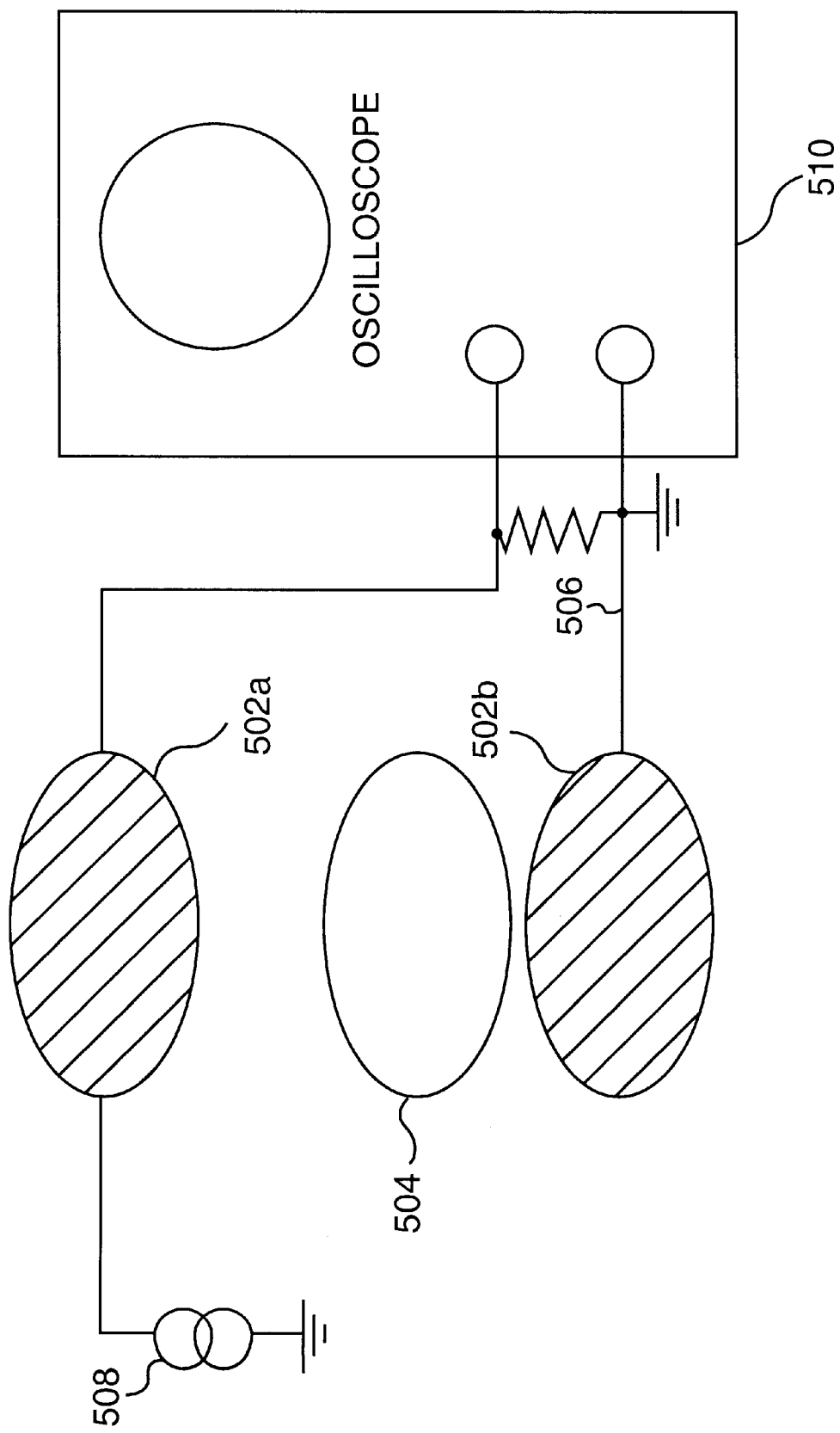
FIG. 2 is a schematic block diagram illustration application of an alternative type of pressure sensor in the system of FIG. 1.

The function of each sensor 104 is to transform tongue, lips, or cheek muscular force into an electrical signal that can be processed and applied to drive a visual display such as one of the LED bargraph displays 320. FIG. 2 illustrates, however, that in addition to an LED bargraph display 320 other graphic or numerical display devices, such as an oscilloscope 510, may be used to display the output from any of the signals on any of the tools. Additionally, a speaker (not shown) may be used in conjunction with LED bargraph display 320 or oscilloscope 510 to provide audible indication.

FIG. 2 also illustrates that sensor 104 may constitute a variable capacitor when employed in a voltage divider measurement circuit as illustrated. The very small capacitance values, such as, for example, less than 10 pfds, associated with a sensor of the size compatible with the measurement area associated with the oral appendages, i.e., lip, tongue, etc., requires that the divider circuit be driven at a relatively high frequency. Control and display device 314 contains device 508 that, in FIG. 2, provides the high frequency signal required to drive the circuit such that it produces a capacitive reactance sufficiently low so that control and display device 314 can have a relatively low input impedance, such as, for example, 1 mega ohm. Such a capacitive sensor can be formed by placing a spongy dielectric material 504 between two metal plates 502a and 502b. Pressure applied to at least one of plates 502a and 502b compresses dielectric material 504 which increases the capacitance value and hence reduces the capacitive reactance.

Figure 3:
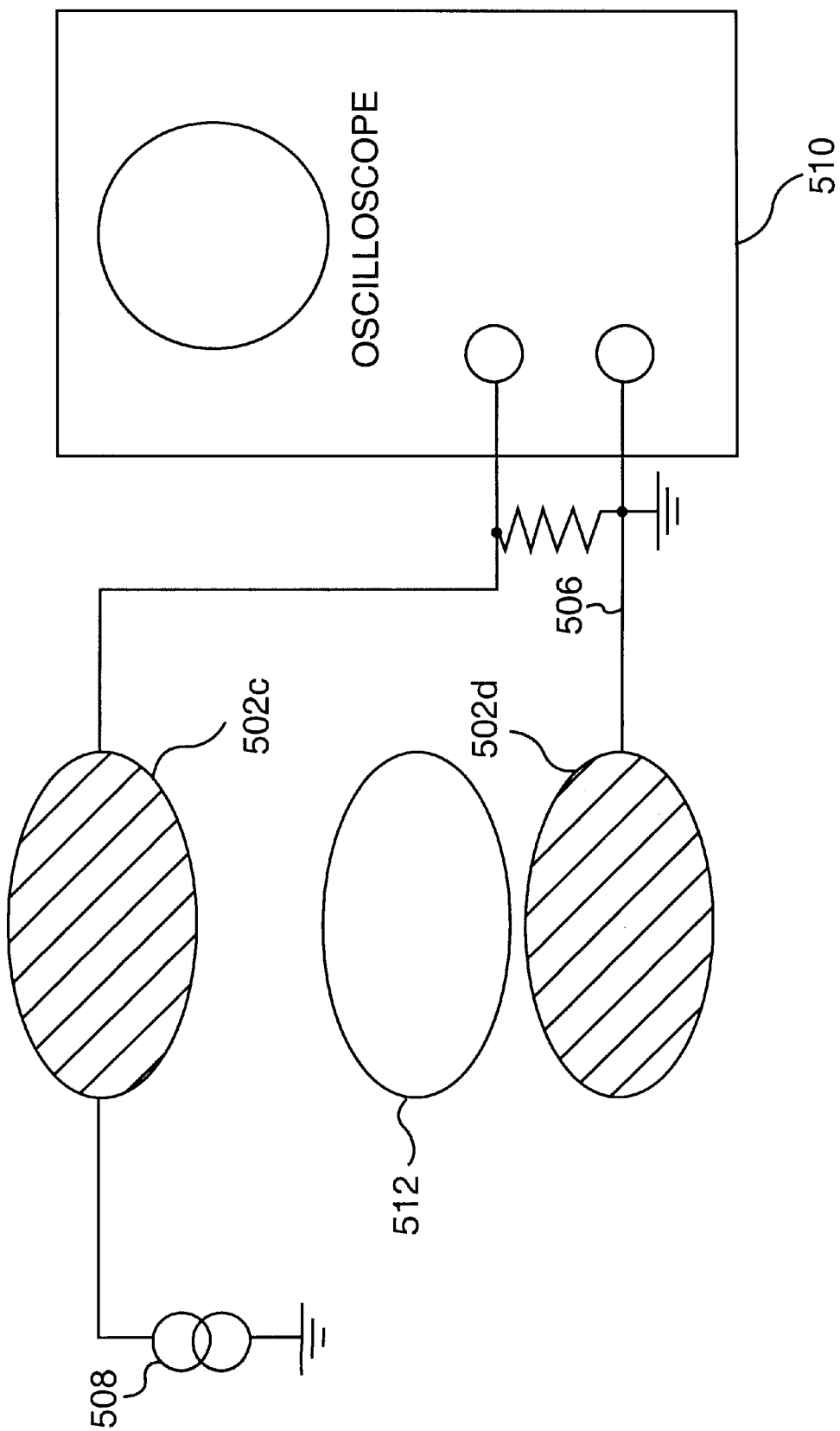
FIG. 3 is a schematic block diagram illustration of a capacitive coupling type of pressure sensor in the system of FIG. 1.

Another sensor 104 is a capacitive coupling device, which is the preferred embodiment. This approach employs a miniature capacitor in the circuit configuration as shown in FIG. 3. In this preferred embodiment, one plate 502c or 502d is the human appendage causing the force to be measured and the other is a metal plate. Additionally, a non-compressible dielectric material 512 is placed between plates 502c and 502d. The change in capacitance is achieved based on the combined area of the capacitor plates 502c and 502d. In other words, the capacitance value of the capacitor varies directly as a function of the area of each of the two capacitor plates. Thus, as the appendage contacts the dielectric material, with a metal plate on the other side, the area of appendage contacting the dielectric increases. Because the dielectric, in this case, does not compress, the capacitance varies in direct proportion to the area covered by the appendage in contact with the dielectric and, thus, the magnitude of the contact force.

As shown in FIGS. 2 and 3, sensors 104 receive a high frequency excitation signal from an oscillator 508 contained in control and display device 314. In the preferred embodiment the excitation signal is approximately 300 kHz. The excitation signal is applied to the voltage divider comprising the sensor 104 and a fix input resistive element 506 of control and display device 314. This produces a voltage across control and display device 314 that is inversely proportional to the capacitive reactance of the sensor 104.

The invention described provides the ability to set thresholds of correctness in applying contact and pressure to the appropriate sensor. These thresholds can be visible along with the performance levels for comparison. Means can be used for recording performance over time. Both the target level and achievement level can be presented and recorded dynamically. Thus, a series of sequential objectives and achieved levels can be presented for evaluation.

Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

What is claimed is:

1. An oral motor therapy exercise tool comprising:
   a handle;
   a mouthpiece connected to the handle and configured for insertion into a patient's mouth, where said mouthpiece is configured to substantially conform to a contour of the patient's palate; and
   at least one pressure sensor included with the mouthpiece at a position that allows the at least one pressure sensor to be contacted by an element of the patient's oral anatomy when the mouthpiece is positioned in the patient's mouth, the at least one pressure sensor comprises: at least one metal plate and a non-compressible dielectric material positioned adjacent the at least one metal plate adaptable so that an oral appendage of the patient is capable of contacting the dielectric material surface whereby a capacitance value can be measured resulting from the contact of the oral appendage and the dielectric material surface which varies as a function of the combined area of the at least one metal slate and the oral appendage contacting surface, wherein a variance in force can be determined in proportion to the relative variation of the combined area upon biting by the patient.

2. The oral motor therapy exercise tool recited in claim 1, further including:
   wiring connected at one end to the at least one pressure sensor and extending through the handle to an external termination; and
   a connector providing the external termination of the wiring from the at least one pressure sensor.

3. The oral motor therapy exercise tool recited in claim 1, wherein the mouthpiece further includes a lip portion.

4. An oral motor therapy system comprising:
   an oral motor therapy tool having a handle, a mouthpiece connected to the handle and configured for insertion into a patient's mouth, where the mouthpiece is configured to substantially conform to a contour of the patient's palate, and at least one pressure sensor included with the mouthpiece at a position that allows the at least one pressure sensor to be contacted by an element of the patient's oral anatomy when the mouthpiece is positioned in the patient's mouth, the at least one pressure sensor comprises: at least one metal plate and a non-compressible dielectric material positioned adjacent the at least one metal plate adaptable so that an oral appendage of the patient is capable of contacting the dielectric material surface whereby a capacitance value can be measured resulting from the contact of the oral appendage and the dielectric material surface which varies as a function of the combined area of the at least one metal plate and the oral appendage contacting surface, wherein a variance in force can be determined in proportion to the relative variation of the combined area upon biting by the patient; the at least one pressure sensor producing a signal indicative of the contact of the at least one pressure sensor to the element of the element of the patient's oral anatomy and varying monotonically with the applied pressure; and
   a display device coupled to the oral motor therapy tool to display the information provided by the at least one pressure sensor.

5. The oral motor therapy system recited in claim 4, further including an electrical signal generator coupled to the pressure sensor to convert the detected force into a corresponding electrical signal where the display device is coupled to the electrical signal generator to convert the electrical signal into a visual display of the detected force.

6. The system recited in claim 4, wherein the display device records a single signal of information provided by at least one of said pressure sensors and compares the recorded single signal to a predetermined standard event.

7. The system recited in claim 4, wherein the display device records a sequence of signals of information provided by at least one of said pressure sensors and compares the sequence of signals to a predetermined standard sequence of events.

* * * * *